United States Patent
Loukipoudis et al.

(10) Patent No.: US 7,411,693 B2
(45) Date of Patent: Aug. 12, 2008

(54) IMAGE DATA DISSEMINATION SYSTEM AND METHOD

(75) Inventors: Evgueni Nikos Loukipoudis, Waasmunster (BE); Raymond Joe Brunsting, Waterloo (CA); Jeffery Frederick Avery, Waterloo (JP)

(73) Assignee: AGFA Inc., Toronto (CA)

( * ) Notice: Subject to any disclaimer, the term of this patent is extended or adjusted under 35 U.S.C. 154(b) by 618 days.

(21) Appl. No.: 10/964,783

(22) Filed: Oct. 15, 2004

(65) Prior Publication Data
US 2006/0082809 A1    Apr. 20, 2006

(51) Int. Cl.
*G06F 15/00* (2006.01)
*G06F 15/16* (2006.01)
*G06Q 50/00* (2006.01)

(52) U.S. Cl. .............. 358/1.15; 705/2; 705/3; 707/1; 707/104.1; 709/217; 709/219

(58) Field of Classification Search ........... 358/1.9, 358/1.14–1.15, 400, 403, 1.12; 705/2–3, 705/14; 370/389; 707/1, 104.1; 709/217, 709/219, 231, 246; 715/721, 838; 348/61, 348/333.05; 382/224; 725/105
See application file for complete search history.

(56) References Cited

U.S. PATENT DOCUMENTS

| | | | |
|---|---|---|---|
| 5,974,201 A | 10/1999 | Chang et al. | |
| 6,349,373 B2 | 2/2002 | Sitka et al. | |
| 6,381,029 B1* | 4/2002 | Tipirneni | 358/1.14 |
| 6,574,629 B1 | 6/2003 | Cooke, Jr. et al. | |
| 6,584,461 B1 | 6/2003 | Patel et al. | |
| 7,251,790 B1* | 7/2007 | Drucker et al. | 705/838 |
| 7,257,832 B2* | 8/2007 | Beane et al. | 725/105 |
| 2002/0016718 A1* | 2/2002 | Rothschild et al. | 705/2 |
| 2002/0186899 A1 | 12/2002 | Bohnenkamp | |

OTHER PUBLICATIONS

Okura, Y. et al, "Journal of Digital Imaging—An Inductive Method For Automatic Generation of Referring Physician Prefetch Rules for PACS", Journal of Digital Imaging, vol. 15, No. 4, pp. 226 to 231, Dec. 2002.

Page, Douglas, "Method Generates Prefetch Rules Automatically", PACSweb website: http://www2.dimag.com/pacsweb/archives/?id=2142, printed Oct. 15, 2003.

(Continued)

*Primary Examiner*—David K Moore
*Assistant Examiner*—Charlotte M Baker
(74) *Attorney, Agent, or Firm*—Bereskin & Parr; Isis E. Caulder

(57) ABSTRACT

An image data dissemination system and method for anticipating user image requests from a user workstation and for locating, transforming and, as necessary, migrating anticipated representations of image data files to a local storage area for efficient access. An anticipated image request is determined based on a number of factors including the image retrieval historical information associated with a user and/or the user workstation. An anticipated representation of the image data file is also determined. An image data file that satisfies the anticipated image request and is in the anticipated representation is then identified, copied and stored in an optimal local storage area. When a user workstation generates the anticipated image request, the corresponding image data file stored on the optimal local storage area is provided the user workstation.

10 Claims, 5 Drawing Sheets

OTHER PUBLICATIONS

Zhou Su et al., "Integrated pre-fetching and replacing algorithm for graceful image caching", IEICE Transactions on Communications Inst. Electron. Inf. & Commun. Eng Japan, vol. E86-B, No. 9, Sep. 2003, pp. 2753-2763.

Su Z et al., "Performance Improvement of Graceful Image Caching by Using Request Frequency Based Prefetching Algorithms", Institute of Electrical and Electronics Engineers, Tencon 2001, Proceedings of IEEE Region 10 International Conference on Electrical and Electronic Technology, Singapore, Aug. 19-22, 2001, IEEE Region 10 Annual Conference, New York, NY: IEEE, US, vol. 1 of 2, Aug. 19, 2001, pp. 370-376.

Hui Lei, et al., "The design and applications of a context service", ACM Sigmobile Computing and Communications Review, vol. 6, No. 4, Oct. 2002, pp. 45-55.

PCT Search Report/Written Opinion mailed on Dec. 23, 2005.

PCT International Preliminary Report on Patentability mailed on Apr. 17, 2007.

* cited by examiner

IMAGE DATA DISSEMINATION SYSTEM AND METHOD

FIELD OF THE INVENTION

This invention relates generally to the field of image display and more particularly to an improved system and method for retrieving image data files from memory locations.

BACKGROUND OF THE INVENTION

Picture Archiving and Communications Systems (PACS) consist of various components to facilitate the management of images from various imaging modalities. It is therefore necessary to efficiently distribute medical images to various users. Pre-fetching and auto-routing are used to predict when an image will be accessed and to therefore place it in a cache or directly at the station where it is expected to be viewed, with the aim of cutting down wait time for an end user requiring a view of a particular image. Many attempts to reduce waiting times for image retrieval have been made.

For example, U.S. Pat. No. 6,574,629 to Cooke, Jr. et al. discloses a PACS that routes relevant prior studies to a reviewing station in contemplation of a scheduled event through pre-fetching. Pre-fetching rules, used to determine which prior studies on the PACS should be retrieved, are stored in memory and may be set and modified by the user. The studies are then placed into an archive station cache and routed to the appropriate station automatically.

Okura et al. ("An inductive Method for Automatic Generation of Referring Physician Prefetch Rules for PACS," J. of Digital Imaging, pp. 226-231, Vol. 15, No. 4, December 2002), discloses an inductive method to generate pre-fetching rules based on practical data from a hospital (e.g. examination histories, previous images requests, etc.) by employing a decision tree algorithm. This avoids the pre-fetching of unnecessary data.

However, since these systems are designed to pre-fetch full fidelity image data, they introduce significant system load since in most applications prior exams do not need to be full fidelity. Also, these systems do not allow for optimization of data traffic across networks and between devices, or for optimization of the size and resolution of image data. As a result, these systems do not adequately address waiting times in the display of images.

SUMMARY OF THE INVENTION

The present invention provides in one aspect, an image data dissemination system for retrieving and displaying an image, said system comprising:

(a) a first storage area for storing an image data file associated with the image;

(b) a user workstation coupled to the first storage area for generating an image request and for displaying the image data file;

(c) a processor coupled to the user workstation and to the first storage area at a first transmission distance, said processor being adapted to receive the image request from the user workstation and to selectively retrieve the image data file from the first storage area, said processor being further adapted to:

(i) maintain an image retrieval history for the user workstation;

(ii) use the image retrieval history to determine an anticipated image request for the user workstation;

(iii) use the image retrieval history to determine an anticipated representation associated with the anticipated image request;

(iv) determine whether the first storage area contains an image data file that satisfies the anticipated image request and is of the anticipated representation;

(v) if (iv) is true, then when the user workstation generates the anticipated image request, provide the corresponding image data file from said first storage area to the user workstation for display.

In another aspect, the present invention provides a method of retrieving and displaying an image within an image data dissemination system having first storage area for storing an image data file associated with the image and a user workstation coupled to the first storage area for generating an image request and for displaying the image, said user workstation being coupled to the first storage area at a first transmission distance, said method comprising:

(a) maintaining an image retrieval history for the user workstation;

(b) using the image retrieval history to determine an anticipated image request for the user workstation;

(c) using the image retrieval history to determine an anticipated representation associated with the anticipated image request;

(d) using the image retrieval history to determine an anticipated representation associated with the anticipated image request;

(e) determining whether the first storage area contains an image data file that satisfies the anticipated image request and is of the anticipated representation;

(f) if (e) is true, then when the user workstation generates the anticipated image request, providing the image data file that satisfies the anticipated image request from said first storage area to the user workstation for display.

BRIEF DESCRIPTION OF THE DRAWINGS

For a better understanding of the present invention, and to show more clearly how it may be carried into effect, reference will now be made, by way of example, to the accompanying drawings which show some examples of the present invention, and in which.

Figure 1:
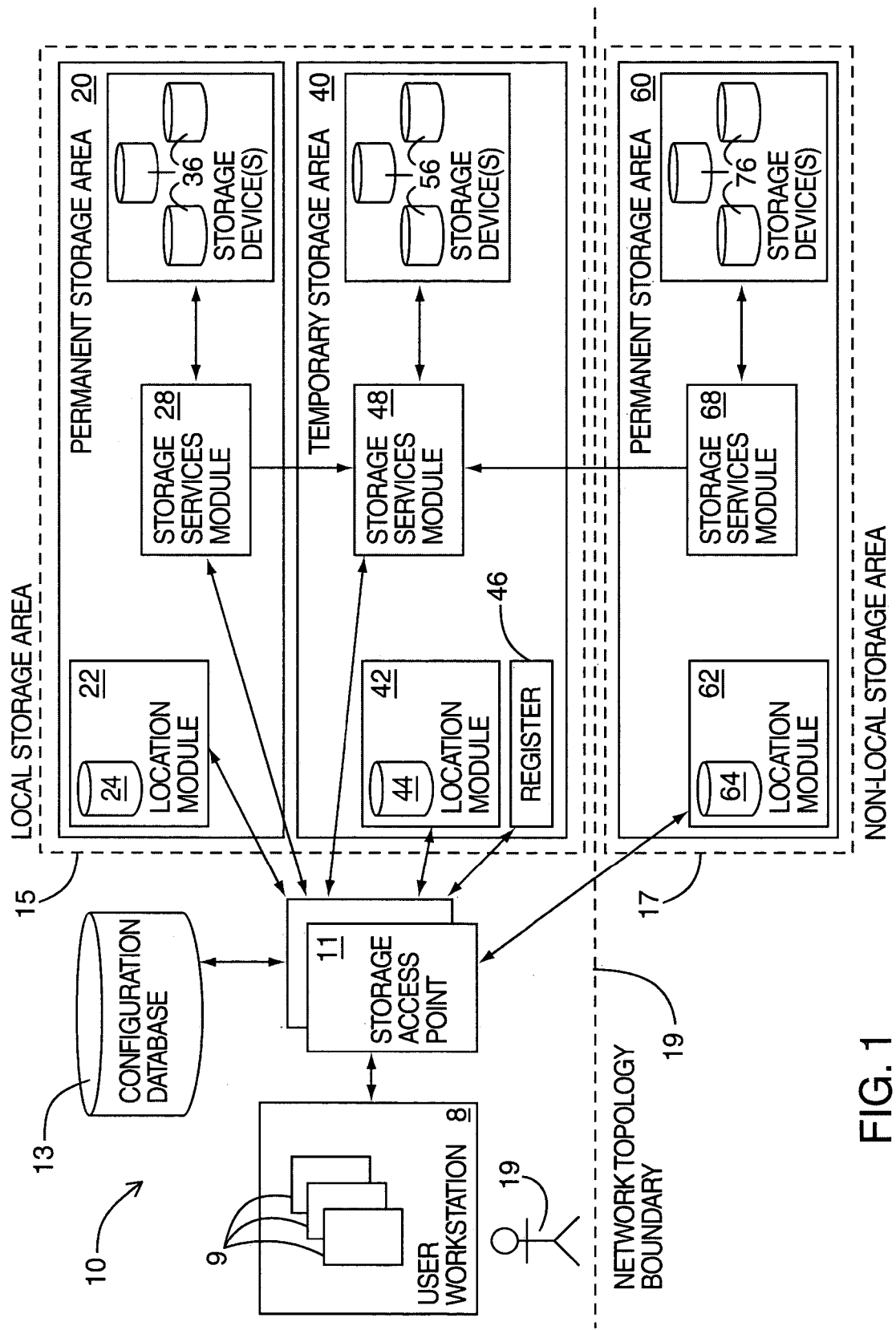
FIG. 1 is a block diagram of the image data dissemination system of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

Figure 2:
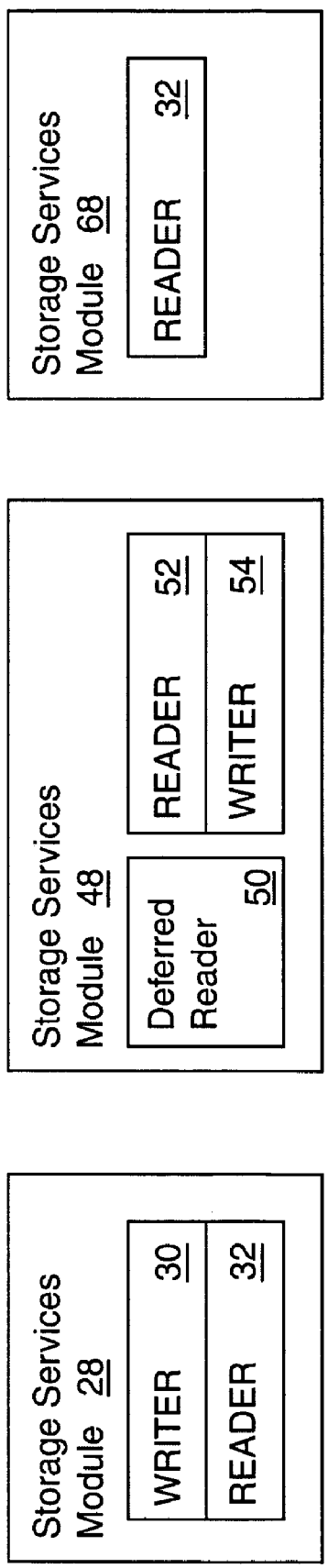
FIG. 2 is a block diagram illustrating in more detail the storage service modules of the image data dissemination system of FIG. 1.

Reference is first made to FIGS. 1 and 2, which illustrate components of an image data dissemination system 10 made in accordance with a preferred example of the invention. Image data dissemination system 10 includes a user workstation 8, a storage access point 11, a local storage area 15 containing permanent storage area 20 and temporary storage area 40 and a non-local storage area 17 that contains a permanent storage area 60. Local storage area 15 and non-local storage area 17 are separated by a network topology boundary 19 as shown.

Image data dissemination system 10 reduces the delay in presenting an image to a user 19 on user workstation 8 by predetermining anticipated image requests and providing image data files that satisfy such image requests within local storage areas at optimal transmissions distances from user workstation 8. An anticipated image request is determined by determining anticipated image requests based on user preferences and historical user activity. Such factors are also used to determine the representation that is likely to be required by user workstation 8. Finally, network and memory characteristics (e.g. file transfer rates, local storage capacity, etc.) are used to determine which local storage areas should be used to serve the image data file that satisfies the anticipated image request and which has the anticipated representation.

User workstation 8 is any computing device that accesses medical image data, including but not limited to, personal computers (PCs), server computers, handheld electronic devices such as personal digital assistants and cell-phones. User workstation 8 is used to access image data files located in either the permanent storage area 20 or 60 or the temporary storage area 40 via the storage access point 11.

In particular, user workstation 8 is adapted to allow a user 19 to select and view image various data files including DICOM data files 9 (e.g. images, waveforms, structured reports, overlays, presentation states, etc.), as well as non-DICOM data files 9 (e.g. dictations, MPEG movies, reports, etc.) It should be understood that in the following discussion, it will be assumed that image data dissemination system 10 is able to identify and predict anticipated image requests for particular users 7 and/or user workstations 8. It is contemplated that this could be achieved in a number of ways.

For example, prediction of image requests could be accomplished through identification of the user workstation 8, and/or the user login identities that typically use the user workstation 8 etc.) Prediction of image requests could also be based on historical usage patterns (e.g. a user 19 may typically use one or two particular workstations). In addition, image data dissemination system 10 may also associate a particular workstation 8 with a particular category of user, a particular type of worklist provided by user 19, or some other indicia that identifies the type of work that is conducted on this station (e.g. whether the particular station is used for CT images). Since each workstation 8 will have certain network/bandwidth capabilities, the particular fidelity that is appropriate for the kind of image data that is being viewed will also be considered by image data dissemination system 10.

Local storage area 15 refers to any number of local permanent storage areas 20 and any number of local temporary storage areas 40 which exist within the same network topology boundary 19 as user workstation 8.

Permanent storage area 20 contains a location module 22, a storage services module 28, and storage devices 36.

Location module 22 contains a location repository 24, which stores the location of all image data files stored in storage devices 36. Location module 22 is used to identify and locate image data files within permanent storage area 20 and interfaces with storage access point 11 to provide access to image data files stored within permanent storage area 20.

Storage services module 28 reads and writes data from storage devices 36 and is shown in greater detail in FIG. 2. Storage services module 28 includes a writer 30 and a reader 32. Writer 30 is used to store new image data files that are created locally. Reader 32 copies locally created image data files from storage devices 36 and provides these image data files to storage access point 11 or storage service module 48 of temporary storage area 40.

Storage devices 36 can be implemented by any direct storage devices that are capable of providing immediate access to stored image data files, such as a redundant array of inexpensive disks (RAID), storage area network/network attached storage (SAN/NAS), a database, high-speed memory (HSM).

Location module 62, storage services module 68 and storage devices 76 of permanent storage area 60 within non-local storage area 17 each function and interact similarly to those of permanent storage area 20 within local storage area 15. Also, as shown in FIG. 2, permanent storage area 60 within non-local storage area 17 uses reader 52 to copy and transfer image data files from storage devices 76 to temporary storage area 40. Permanent storage area 60 also users writer 54 to store new image data files that are created locally. It should be understood that in the following discussion, any described interaction between a device within local storage area 15 and a device within non-local storage area 17 is representative of an interaction between a device within local storage area 15 with any device located within a non-local storage area 17 located outside the network topology boundary 19.

Temporary storage area 40 functions in a similar manner to the above-mentioned permanent storage area 20, with two notable exceptions.

The function of permanent storage area 20 is to store "derived representations" or "copies" of original image data files for an indefinite length of time. The function of temporary storage area 40 is to provide a temporary cache of image data files transferred locally (e.g. from the permanent storage area 20 of the local storage area 15) or migrated from external storage areas (e.g. permanent storage area 60 of the non-local storage area 17). Accordingly, storage devices 56 within temporary storage area 40 contain image data files created locally within a local storage area 15 and/or imported from a non-local storage area 17.

The capabilities of storage services module 48 reflect this. That is, in addition to storing the location of all temporary storage area-stored image data files in location module 42, storage services module 48 records the originating location of all stored image data files in a register 46. Also, register 46 is used to locate all image data files that are "related" to each other (i.e. associated with a the same patient, part of the same study, etc.) Storage devices 56 of temporary storage area 40 may be any conventional high-speed memory device or another type of rapidly accessible memory storage. As shown in FIG. 2, temporary storage area 40, by virtue of its role in hosting migrated image data files, includes reader 52 and writer 54 which are used to read from and write to, respectively, storage devices 56.

Temporary storage area 40 also includes a storage services module 48 (FIG. 2) that uses a deferred reader 50, to achieve asynchronous data transfers from readers of storage devices other than those of temporary storage area 40. Deferred reader 50 communicates with storage access point 11, using information received from the communication to perform image data file manipulation (e.g. in-line format conversion, frame selection, etc.) where required by image data dissemination system 10. This manipulation creates new representations of image data files.

Permanent storage areas 20 and 60 host a single master copy of all image data files created at that location. It should be understood that permanent storage area 16 does not store any representations or copies of original image data files. Rather, permanent storage area 16 either contains the original version of an image data file or nothing at all (i.e. when the image data file is deemed suitable for deletion). Original image data files stored within permanent storage area 16 are typically backed up for damage recovery retrieval purposes (e.g. tape backups stored off-site).

Although only one master copy of an image data file may exist within permanent storage area 20 of the image data dissemination system 10 at any moment, temporary storage area 40 may host different representations of the same image data file and these representations will remain in the temporary storage area indefinitely. Multiple temporary storage areas 40 may host multiple instances (i.e. identical copies) of an image data file.

Also, it should be understood that the permanent storage areas 20 operate independently from temporary storage areas 40. That is, it is possible for an image data dissemination system 10 to delete a master copy of image data file in the permanent storage area 20 but to leave derived image data files in the temporary storage area 40 when only low-fidelity images are required. In the case where a study is determined to be no longer clinically relevant, it is contemplated that image data dissemination system 10 would delete associated image data files in both the permanent and temporary storage areas 20 and 40.

Storage access point 11 is a server process that facilitates communication between the user workstation 8 and local and non-local storage areas 15, 17. Storage access point 11 is responsible for migrating image data files stored in non-local permanent storage area 60 to the geographically closer temporary storage area 40. Where image data dissemination system 10 anticipates that an image request is likely, as will be described, storage access point 11 will locate an image data file that best corresponds to the corresponding image data file and migrate the corresponding image data file to temporary storage area 40 of local storage area 15 for efficient access by user workstation 8.

Referring back to FIG. 1, location modules 22, 42, 62 are used to identify and locate corresponding image data files that relate to image requests. Then, when image data dissemination system 10 determines an anticipated image request, storage access point 11 will seek out the image data file or series of image data files (i.e. containing the requested image data file along with "related" image data files) that will best satisfy the anticipated image request. Storage access point 11 preferably maintains information about prior image data file retrievals and transformations (i.e. how an image data file has been altered) for purposes of optimizing placement of derived image data files within temporary storage area 40.

Once an image request has been received, configuration database 13 is initially queried to identify all of the metadata associated with an exam. The clinical database will include the unique identifier that is sent to the storage access point 11 (and later to the location modules) for lookup later. The storage access point 11 will check to see whether a corresponding image data file is already stored in temporary storage area 40. If not, then storage access point 11 will query local and non-local permanent storage area 20 and 60. If temporary storage area 40 is found to contain another representation of the corresponding image data file then register 46 locates and gathers this and all other related corresponding image data files. In various examples of the invention, location queries may be conducted by storage access point 11 by checking a centralized or redundant local location repository, or by checking a pre-specified group of storage host location repositories.

Storage access point 11 queries configuration database 13 to determine the characteristics (e.g. representation, location, instance, etc.) associated with a corresponding image data file to be migrated. When image data dissemination system 10 determines a particular anticipated image request it also determines an anticipated representation to associate with the image request. Then storage access point 11 locates a corresponding image data file that best satisfies the image request. Storage access point 11 then determines whether the corresponding image data file is in the anticipated representation or not. Where the anticipated representation associated with the anticipated image request does not match the current representation of the corresponding image data file, storage access point 11 triggers a transformation process to transform the corresponding image data file into the anticipated representation. This transformation process can include the use of a notification message to inform the user 19 when the newly formatted image data file is available. To service a plurality of users and/or for failover, storage access point 11 may also exist as a plurality of instances.

In one example of the invention, a user 19 may request an image data file that is stored in a plurality of local and non-local storage areas 15, 17. Individual storage areas 15, 17 may contain a variety of storage units that contain individual image data files and/or a plurality of image data files that are associated with the image data file being requested by user 19. Where individual image data files are considered to be "related" (e.g. created or modified as part of a related study or at the same time for a specific patient), all related image data files may be grouped as a series. The series would then represent a single unit of storage.

For example, when user workstation 8 sends a request to storage access point 11 to retrieve a single image data file that is part of a series, the request will result in the entire series being migrated to temporary storage area 40 within local storage area 15. It will be understood that any granularity of data storage and method of data transfer may be utilized within image data dissemination system 10.

Figure 3:
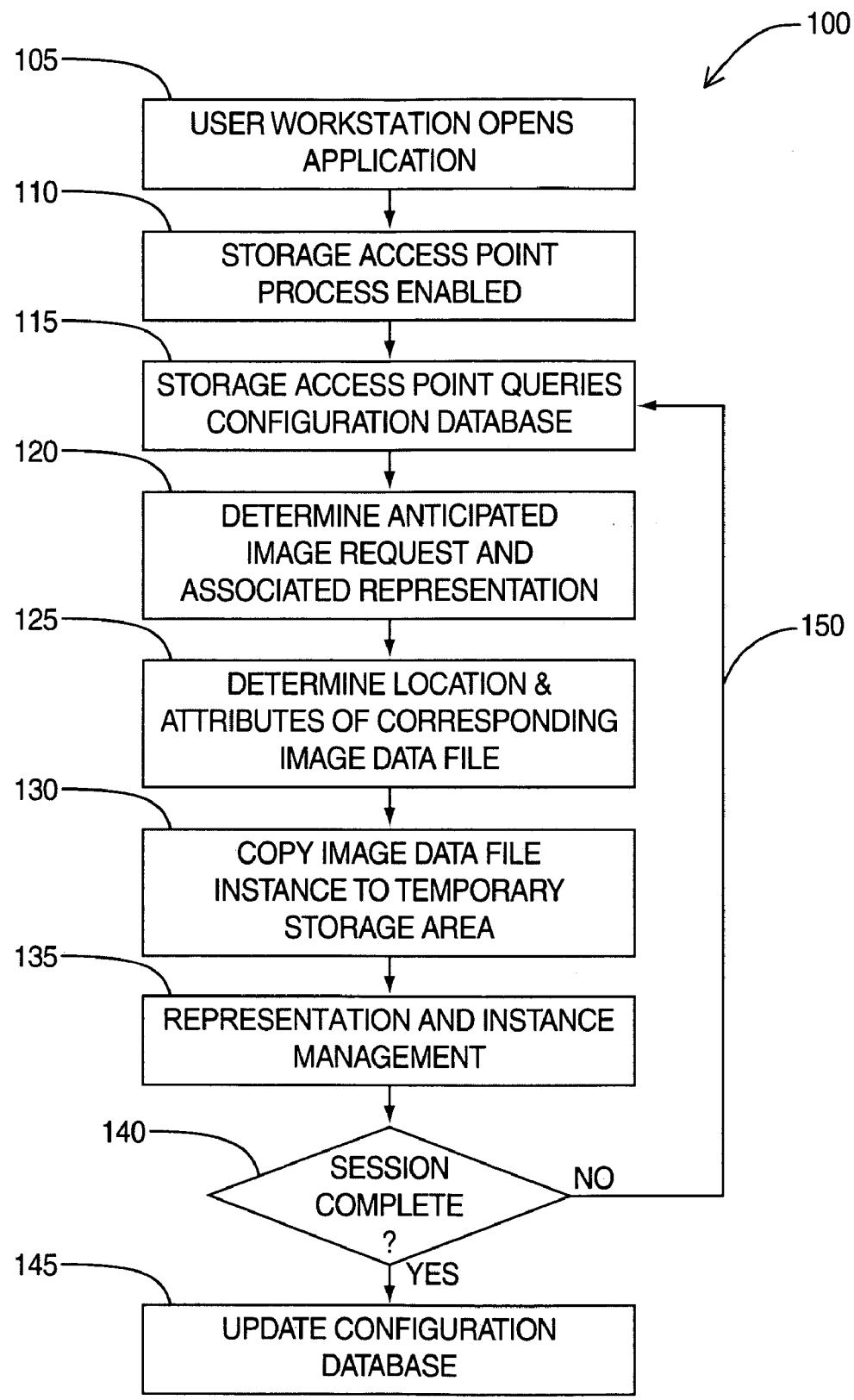
FIG. 3 is a flowchart illustrating the general operational steps of the image data dissemination system of FIG. 1.

Referring now to FIGS. 1, 2 and 3, the basic operation of an example of image data dissemination system 10 of the present invention will be discussed. Specifically, FIG. 3 illustrates the basic operational steps 100 executed by the image data dissemination system 10.

At step (105), a user 19 at user workstation 8 opens an application or activates a device that will issue image data file requests. At step (110), storage access point 11 is enabled and queries the configuration database 13 at step (115) to determine various characteristics associated with user 19 (e.g. user system clearance level, user preferences, user image data file retrieval history etc.) and/or user workstation 8 (e.g. image retrieval history, display resolution specifications, etc.).

At step (120), the information obtained at step (115) is used to determine anticipated image request, that is to predict which image data files will be requested for viewing by user 19 at user workstation 8. Specifically, it is determined which particular images are likely to be requested given a particular request (or a historical pattern of requests) from user workstation 8. This is accomplished using information obtained from step (115) relating to user characteristics as well as information associated with current session requests received from user workstation 8 (e.g. that head body part image data files have been viewed from 1 to 3 PM every Tuesday) to predict future image requests (e.g. that more head body image data files will be requested at these times).

As discussed above, it is assumed that image data dissemination system 10 will be able to associate the identity of a particular user 19 with image data file requests. In addition, it will be assumed that image data dissemination system 10 is able to monitor and predict the whether particular user workstations 8 are being used by various users 7 using historical information and time-of-day event monitoring. In this way, it is possible to anticipate image requests from various users of the image data dissemination system 10 for user workstation 8 (i.e. devices).

At step (125), once an anticipated image request has been determined, image data dissemination system 10 locates the corresponding anticipated or "likely to be requested" image data files as ascertained at step (120) within permanent and temporary storage areas 20 and 40 and determines the physical location and other related attributes associated with such image data files. The specific process steps associated with determining the physical location and attributes of such image data files will be discussed in respect of FIG. 4.

Image data dissemination system 10 then determines the anticipated representation, that is the "likely to be desired" representation for each anticipated image data file. The anticipated representation of an image data file will be determined by study related characteristics (e.g. modality type, body part, etc.) as well as station related characteristics (e.g. station image rendering ability, etc.).

Image data dissemination system 10 uses the user selection history associated with user workstation 8 to determine the anticipated representation for an image data file. This is accomplished by determining what representations of images (i.e. formats, body part type, etc.) are likely to be desired. Returning to the example discussed above, if a physician routinely requests CT type image data files on a particular workstation from 1 to 3 PM, image data dissemination system 10 will use this information to ensure that appropriate representations of image data files (i.e. suitable for viewing by a physician in CT format) are available within a local permanent or temporary storage area 20, 40 at times of the day (i.e. 1 to 3 PM) when the physician is likely to make such requests.

Selection of the anticipated representation of an image data file from amongst related representations the image data file located in different locations (i.e. on various permanent and temporary storage areas 20, 40) is based on various factors including user preferences, exam type, and network topology. For example, if the request is being made by a clinician to view a prior exam then the system will preferentially select a compressed version of the image data file that is stored in a location that is a short "transmission distance" from the requesting workstation. On the other hand, if the request is being made for a new exam (not reported yet) by a radiologist, then the system will preferentially select a lossless compressed version of the image that is stored in a location (i.e. likely a permanent storage area 20) that is a short "transmission distance" from the requesting workstation.

Also at step (125), image data dissemination system 10 considers the optimal storage area from which to serve the anticipated representation of the image data file to user workstation 8. This determination will be made based on the "transmission distance" between the storage area being considered and the user workstation 8. It should be understood that the term "transmission distance" as it is being used here represents a measure of the desirability of transmission of an image data file from a particular storage area to the user workstation 8.

For example, the "transmission distance" a particular storage area to the user workstation 8 could represent the physical distance that the image data file needs to be transmitted the particular storage area to the user workstation 8. However, the term "transmission distance" could more generally various factors taken alone or in combination, such as: workstation characteristics, network characteristics, and study characteristics. These types of factors are all considered in order to determine the optimal location (i.e. within which local permanent or temporary storage area 20, 40) from which to serve the anticipated representation of the image data file to user 19 at user workstation 8. A variety of file size, memory and network capacity related characteristics are considered and prioritized by image data dissemination system 10 at this stage.

Image data dissemination system 10 scrutinizes the various characteristics associated with user workstation 8 (e.g. memory capacity and availability) in order to determine what storage capacity is available locally. Network characteristics are also considered, including the transmission cost (i.e. possibly related to physical distance) associated with transporting the image data from a particular storage area to another storage area or user workstation 8. Since network characteristics typically fluctuate throughout the day, the system needs to react to changing network conditions either dynamically or on a scheduled basis. Finally, study characteristics are also considered by image data dissemination system 10. Depending on the type of study being requested by user 19, image data dissemination system 10 will determine how transmission of the image data can be optimally conducted (e.g. how much compression can an image data file tolerate, what presentation format is required, etc.)

At step (130), once the location and attributes of the anticipated representation of the image data file are determined at step (125), an instance of this representation of the image data file is created in deferred reader 50 of temporary storage area 40. The originating source of the created instance is dependent upon the location of the corresponding image data file determined at step (125).

If the anticipated representation of the image data file resides at non-local storage area 17, the image data file is copied (i.e. another instance is created) from permanent storage area 60 to temporary storage area 40. Storage access point 11 passes a request to reader 70 at storage services module 68 of permanent storage area 60 for the anticipated representation of the data image data file (or image data file series). In a network configuration permitting direct requests, storage access point 11 passes this request directly to storage services module 68. It should be noted that while this "direct" approach may be faster, it may also result in a more complex set of communication paths between various components of image data dissemination system 10. Alternatively, storage access point 11 may communicate to a storage access point process (not shown) at non-local storage area 17, which in turn would pass the request to storage services module 68. Reader 70 retrieves the anticipated representation of the image data file from storage devices 76 and passes the corresponding image data file to deferred reader 50 of storage services module 48.

If the anticipated representation of the image data file is found to reside in storage devices 36 of permanent storage area 20, then an instance of the anticipated representation of the image data file is created within deferred reader 50 of temporary storage area 40 by copying the image data file from permanent storage area 20 via reader 32 of storage services 28. Similarly, where the anticipated representation of the image data file is found to reside in storage devices 56 of temporary storage area 40, an instance of the anticipated representation of the image data file is copied to deferred reader 50 of temporary storage area 40. In an example of the invention, permanent storage area 20 may be designed to pass local image data files directly to user workstation 8 via storage access point 11. In another example of the invention, temporary storage area 40 may be implemented as high speed memory, thus making it advantageous for all image data files to be passed to user workstation 8 from temporary storage area 40.

At step (135), once the anticipated representation of the image data file has been read by, and copied to, deferred reader 50 on temporary storage area 40, representation and instance management reformats the corresponding image data file as needed. The specific process steps associated with further transforming the image data file into a desired format will be discussed in further detail in respect of FIG. 5.

After the corresponding image data file has been pre-fetched into deferred reader 50 of temporary storage area 40, and transformed into the appropriate format, at step (140) it is determined whether the session is complete or additional image data files (i.e. "related" image data files) are to be retrieved. In the case where another image data file needs to be pre-fetched, steps (115-135) are repeated.

Once the session is complete, configuration database 13 is updated with recent preferences and user history at step (145) and the pre-fetched image data files are stored in storage devices 56 of temporary storage area 40 for future retrieval purposes by user workstation 8. In another example of the invention, preference and user history updates and storage may occur dynamically for each particular image data file at step (150) as the user is interacting with image data dissemination system 10.

Figure 4:
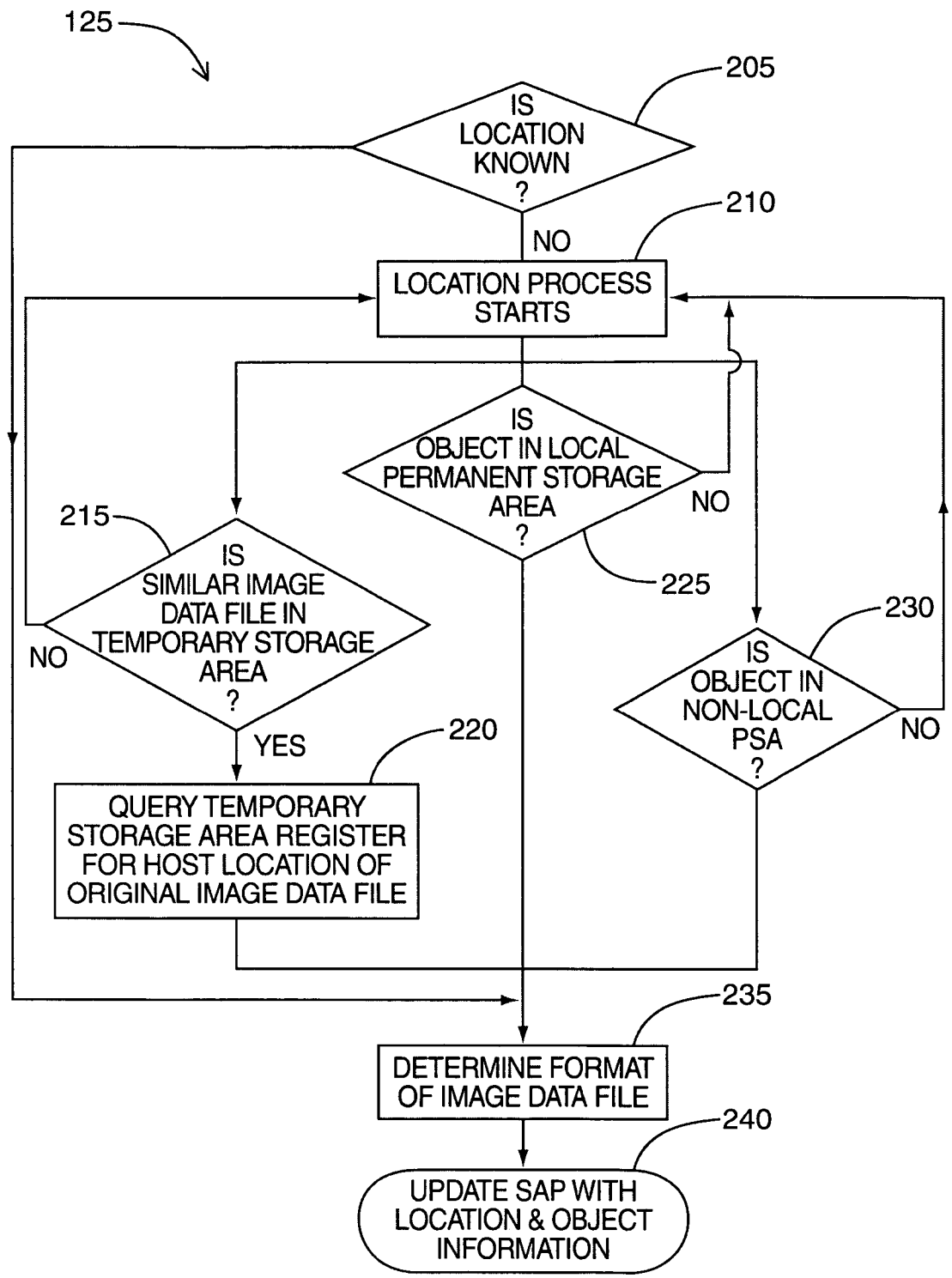
FIG. 4 is a flowchart illustrating the process steps conducted by the image data dissemination system of FIG. 1 to determine the location and attributes associated with a corresponding image data file; and, FIG. 5 is a flowchart illustrating the process steps conducted by the image data dissemination system of FIG. 1 to transform a corresponding image data file into a desired format.

FIG. 4 is a flowchart diagram that illustrates the process steps (125) executed by image data dissemination system 10 to determine the location and attribute information associated with the anticipated image data files discussed above.

At step (205), storage access point 11 is queried to determine if the location of such an image data file is already known. The location of the image data file could be known, for example, if the image data file had already been transferred to temporary storage area 40 in an earlier pre-fetch and was still residing in storage devices 56.

If the location of the image data file is not known, then at step (210), a location process is initiated to locate a corresponding image data file. It should be understood that at this point, no image data files that would satisfy the anticipated image request have been located within temporary storage area 40. Three sample searches are shown at steps (215), (225), and (230). It should be understood that these searches could be performed sequentially or concurrently.

At step (215), storage access point 11 queries location module 42 of temporary storage area 40 for any image data files that are similar to the anticipated image data file. Such a query may involve searching location database 44 for image data files with associated identifiers/characteristics that are similar to the corresponding image data file in question (e.g. same patient name). If at step (215), a similar image data file is not found at temporary storage area 40, the search of this storage area is abandoned and this status (e.g. 'no file located') is returned to the location process by storage access point 11.

If a similar image data file is found, storage access point 11 queries register 46 of temporary storage area 40 to determine the location of the similar image data file. Image data file attributes (i.e. format) are determined at step (235), and image data file characteristics and location information is passed to storage access point 11 at step (240). Location management logic (210) uses this information to query the permanent storage areas 20 and 60.

At step (225), location module 22 queries location database 24 of permanent storage area 20. At step (230), location module 62 queries location database 64 of non-local permanent storage area 60. If a corresponding image data file is found in one of the queried permanent storage areas 20 or 60, then at step (235), characteristics associated with the corresponding image data file are determined. Although geographically displaced, possible queries to local permanent storage area 20 and non-local permanent storage area 60 follow a similar process to that of temporary storage area 40. Any procedural differences are related primarily to communication differences that are inherent in crossing network topology boundary 19.

Characteristics and location information associated with the located corresponding image data file are then passed to storage access point 11 at step (235) for future retrieval.

If no such image data file is found, then the location process is notified. It will be understood that where a centralized location module is employed, all such queries may take place in a single database lookup. Examples of characteristics of interest associated with an corresponding image data file include image size, image resolution, image file type, visual enhancements in an image.

At step (240), the location information and the various characteristics determined in step (235) are stored in storage access point 11 for a future anticipated transfer of the image data file to user workstation 8.

Figure 5:
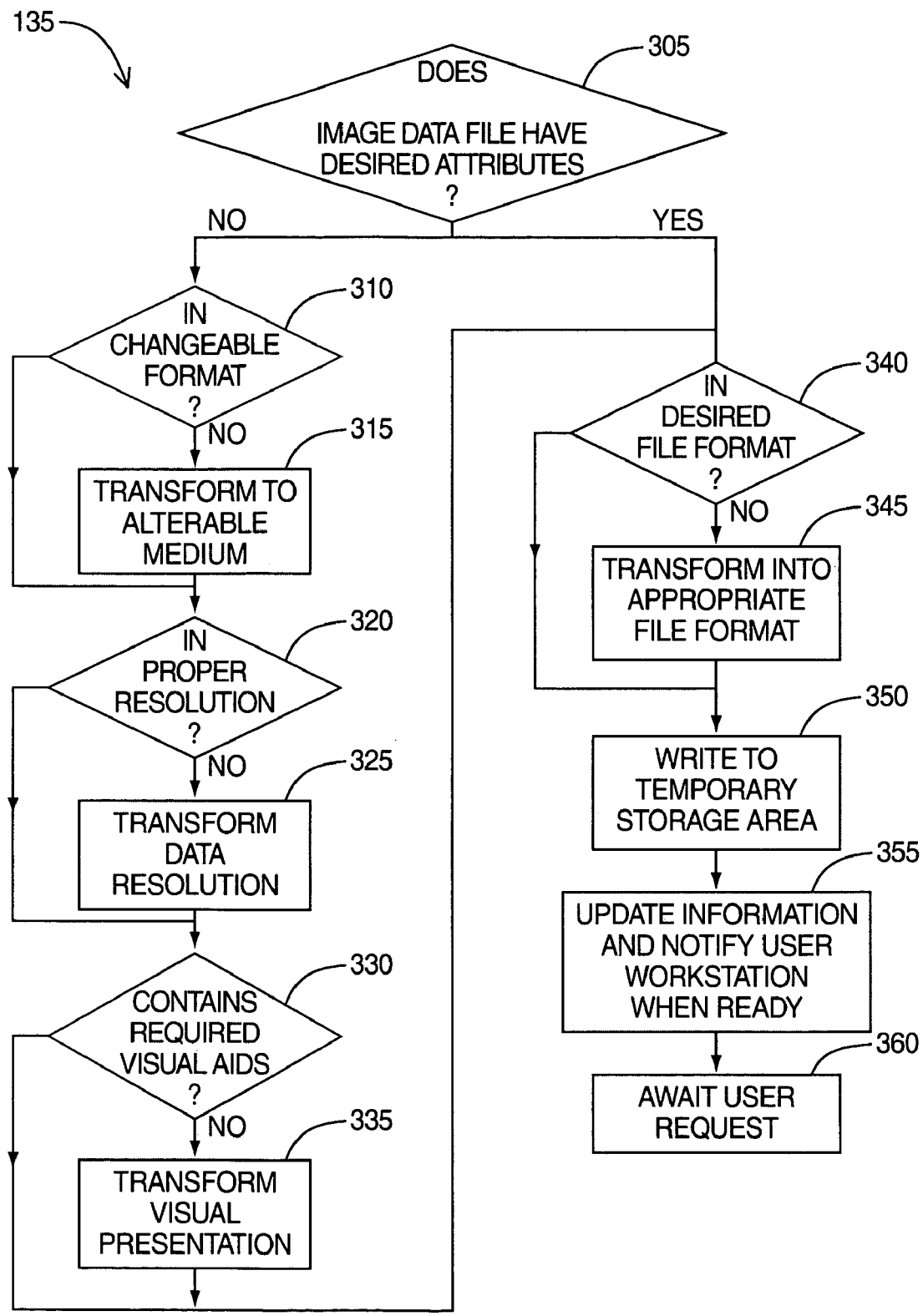

FIG. 5 is a flowchart diagram that illustrates the process steps (135) executed to reformat the located representation of the image data file into a desired format. At step (305), it is determined whether the format of the corresponding image data file is desired (i.e. does the image data file have the desired attributes). In one example of the invention, the appropriateness of the representation is ascertained using descriptive status tags associated with the corresponding image data file. When changes to the representation of the image data file are required, the image data file is altered as necessary. This is achieved by performing various comparisons and related transformations, some examples of which will be described.

For example, at step (310), it is determined whether the located representation of the image data file is in an immediately changeable format. If not then the corresponding image data file is changed to an alterable medium. As is conventionally known, some compression algorithms (e.g. JPEG 2000) allow an image to be compressed such that a lower quality version of the image can be obtained by removing the end portion of the image data file. It is contemplated that at step (310), the located representation of the image data file could be transformed into such a format if they are not already stored in such a format.

At step (320), it is determine whether the corresponding image data file is in an appropriate resolution. If not, then the data resolution level is adjusted within the corresponding image data file. Some original images are very high resolution (e.g. several thousand pixels high and wide) resulting in very large image files. While high-resolution supports advanced image processing algorithms to be applied during diagnosis, the higher resolution images may not be required for non-diagnostic purposes (e.g. viewing as a prior exam). An example of what could be done at this step is reducing the number of rows and columns in an image by 50%, therefore reducing the total number of pixels by 75%.

At step (330), it is determined whether the corresponding image data file contains the necessary visual aids or adjustments (e.g. overlaid text, contrast adjustments, etc.) and if not then the characteristics associated with the visual presentation of the corresponding image data file are altered. During diagnosis both manual and automated tools may be used to detect, measure and highlight interesting artifacts in the image that are related to the diagnosis. Such "visual aids" or "image adjustments" may be externally recorded (e.g. in the configuration database 13), but may not be directly applied to the image data file. At step (330), the image may be transformed in such a way as to directly apply such "visual aids" and "image adjustments" to the image data file for future use. This would allow future workstation to take see the "visual aids" and "image adjustments" even though they may not be sophisticated enough to apply them to the original image data file.

When the necessary transformations have been completed, at step (340), the corresponding image data file is checked to ensure it is in the required file format. If not, then the corresponding image data file is transformed at step (345) such that the data is changed into the desired file format. As discussed above, it should be ensured that image data file is in a format such as JPEG2000 that will offer maximum flexibility as far as future viewing and transformation options are concerned.

It should be understood that any type of image or data manipulation that is employed by medical or general pre-fetching applications may be used in addition to, in combination with, or in place of those mentioned above. For example, replacement of an entire (large) series of images with a smaller series of images consisting of a subset of the original images or what is called "image sub-sampling" is used to handle newer exam types such as thin-slice CT or MR exams where thousands of images are acquired for a single exam. This approach could be implemented within image data dissemination system 10 by storing multiple representations of an image data file (i.e. the "sub-samples") within various local temporary storage areas 40 and using the functionality of image data dissemination system 10 discussed above to manage and deliver selected representations (e.g. every $100^{th}$ "sub-sample", etc.) to user workstation 8.

At step (350), the corresponding image data file is then written to storage devices 56 of temporary storage area 40 using writer 54 of storage services 48. Storage access point 11 is then updated with formatting and availability information. At step (355), user workstation 8 may be notified. Then at step (360), a request from user workstation 8 via storage access point 11 for the corresponding image data file at issue is awaited.

While certain features of the invention have been illustrated and described herein, many modifications, substitutions, changes and equivalents will now occur to those of ordinary skill in the art. It is, therefore, to be understood that the appended claims are intended to cover all such modifications and changes as fall within the true spirit of the invention.

The invention claimed is:

1. An image data dissemination system for retrieving and displaying an image, said system comprising:
   (a) a first storage area for storing an image data file associated with the image;
   (b) a user workstation coupled to the first storage area at a first transmission distance for generating an image request and for displaying the image data file;
   (c) a processor coupled to the user workstation and the first storage area, said processor being adapted to receive the image request from the user workstation and to selectively retrieve the image data file from the first storage area, said processor
      (i) maintaining an image retrieval history for the user workstation;
      (ii) using the image retrieval history to determine an anticipated image request for the user workstation;
      (iii) using the image retrieval history to determine an anticipated representation associated with the anticipated image request;
      (iv) determining whether the first storage area contains an image data file that satisfies the anticipated image request and is of the anticipated representation; and
      (v) if (iv) is true, then when the user workstation generates the anticipated image request, providing the image data file that satisfies the anticipated image request from said first storage area to the user workstation for display.

2. The system of claim 1, further comprising a second storage area coupled to the user workstation at a second transmission distance greater than the first transmission distance, wherein the processor:
   (vi) if (iv) is false then determining whether the second storage area contains an image data file that satisfies the anticipated image request and whether the image data file that satisfies the anticipated image request is of the anticipated representation;
   (vii) if (vi) is true, then copying the image data file that satisfies the anticipated image request from the second storage area to the first storage area and executing (v).

3. The system of claim 1, wherein the processor:
   (viii) determines if the image data file that satisfies the anticipated image request is in a desired format; and
   (ix) if (viii) is false then transforms the image data file that satisfies the anticipated image request into the desired format.

4. The system of claim 1, said first and second storage areas further comprising:
   (A) a memory for storing an image data file that satisfies the anticipated image request; and
   (B) a means to store and retrieve the image data file that satisfies the anticipated image request from the memory.

5. The system of claim 1, wherein said processor uses the image retrieval history along with at least one of the group consisting of user preferences, viewing history, patient information, image status, imaging modality to determine the anticipated image request.

6. A method of retrieving and displaying an image within an image data dissemination system having first storage area for storing an image data file associated with the image and a user workstation coupled to the first storage area for generating an image request and for displaying the image, said user workstation being coupled to the first storage area at a first transmission distance, said method comprising:
   (a) maintaining an image retrieval history for the user workstation;
   (b) using the image retrieval history to determine an anticipated image request for the user workstation;
   (c) using the image retrieval history to determine an anticipated representation associated with the anticipated image request;
   (d) determining whether the first storage area contains an image data file that satisfies the anticipated image request and is of the anticipated representation; and (e) if (d) is true, then when the user workstation generates the anticipated image request, providing the image data file that satisfies the anticipated image request from said first storage area to the user workstation for display.

7. The method of claim 6, wherein the image data dissemination system further comprises a second storage area coupled to the user workstation at a second transmission distance being greater than the first transmission distance, further comprising:

(f) if (d) is false then determining whether the second storage area contains an image data file that satisfies the anticipated image request and whether the image data file that satisfies the anticipated image request is of the anticipated representation;

(g) if (f) is true, then copying the image data file that satisfies the anticipated image request from the second storage area to the first storage area and executing (e).

8. The method of claim 6, further comprising:

(h) determining if the image data file that satisfies the anticipated image request is in a desired format; and (i) if (h) is false then transforming the image data file that satisfies the anticipated image request into the desired format.

9. The method of claim 6, wherein said first and second storage areas further comprise:

(A) a memory for storing an image data file that satisfies the anticipated image request; and (B) a means to store and retrieve the image data file that satisfies the anticipated image request from the memory.

10. The method of claim 6, further comprising using the image retrieval history along with at least one of the group consisting of user preferences, viewing history, patient information, image status, imaging modality to determine the anticipated image request.

* * * * *